US007195909B2

(12) United States Patent
Klenerman et al.

(10) Patent No.: US 7,195,909 B2
(45) Date of Patent: Mar. 27, 2007

(54) MEASUREMENT AND USE OF MOLECULAR INTERACTIONS

(75) Inventors: David Klenerman, Cambridge (GB); Victor Petrovich Ostanin, Cambridge (GB); Fedor Nikolaievich Dultsev, Novosibirsk (RU)

(73) Assignee: Akubio Limited (GB)

( * ) Notice: Subject to any disclaimer, the term of this patent is extended or adjusted under 35 U.S.C. 154(b) by 604 days.

(21) Appl. No.: 10/350,892

(22) Filed: Jan. 24, 2003

(65) Prior Publication Data

US 2003/0194697 A1  Oct. 16, 2003

Related U.S. Application Data

(63) Continuation of application No. 09/700,485, filed as application No. PCT/GB00/01587 on Apr. 25, 2000, now Pat. No. 6,589,727.

(30) Foreign Application Priority Data

Apr. 22, 1999  (GB) ................................ 9909308.0

(51) Int. Cl.
*C12M 3/00* (2006.01)
(52) U.S. Cl. .................. 435/287.2; 422/55; 422/82.05; 435/5; 435/6; 435/7.2; 435/7.32; 435/288.7; 435/808; 436/518; 436/524; 436/527; 436/164; 436/805; 310/311; 310/312; 310/313 R; 310/340
(58) Field of Classification Search .................... None
See application file for complete search history.

(56) References Cited

U.S. PATENT DOCUMENTS 4,236,893 A * 12/1980 Rice ............................ 436/513
4,242,096 A * 12/1980 Oliveira et al. ............. 436/500
4,314,821 A * 2/1982 Rice ............................ 436/540
4,735,906 A * 4/1988 Bastiaans ..................... 436/527
4,999,284 A * 3/1991 Ward et al. ..................... 435/4

(Continued)

FOREIGN PATENT DOCUMENTS

WO    WO 9840739    9/1998

(Continued)

OTHER PUBLICATIONS

Kolomenskii, Al. A. et al., "Interaction of Laser-Generated Surface Acoustic Pulses With Fine Particles: Surface Cleaning and Adhesion Studies", *Journal of Applied Physics*, 1998, pp. 2404-2410, vol. 84, No. 5.

(Continued)

*Primary Examiner*—Christopher L. Chin
(74) *Attorney, Agent, or Firm*—Saliwanchik, Lloyd & Saliwanchik

(57) ABSTRACT

The subject invention pertains to a method for determining the affinity between binding partners, or a property of one of the binding partners dependent on the affinity, comprising the steps of:
 (i) contacting the binding partners, one of which is immobilised on a surface;
 (ii) oscillating the surface at increasing amplitude; and
 (iii) detecting a dissociation event.
An analogous method can be used to separate a target analyte from a composition. The subject invention also pertains to an apparatus for determining the affinity between binding partners, and comprises: a surface (10) having one binding partner (16) immobilised thereon; means for oscillating the surface at increasing amplitude; and means (14, 15) for detecting a dissociation event.

33 Claims, 8 Drawing Sheets

U.S. PATENT DOCUMENTS

| | | | |
|---|---|---|---|
| 5,501,986 A * | 3/1996 | Ward et al. | 436/525 |
| 5,552,274 A | 9/1996 | Oyama et al. | |
| 5,814,525 A * | 9/1998 | Renschler et al. | 436/524 |
| 6,086,821 A | 7/2000 | Lee | |
| 6,368,553 B1 | 4/2002 | Lee | |
| 6,630,309 B2 * | 10/2003 | Willner et al. | 435/7.1 |
| 6,764,860 B2 | 7/2004 | Lee | |

FOREIGN PATENT DOCUMENTS

| | | |
|---|---|---|
| WO | WO 9845692 | 10/1998 |

OTHER PUBLICATIONS

Kurosawa, S. et al., "Latex Piezoelectric Immunoassay: Detection of Agglutination of Antibody-Bearing Latex Using a Piezoelectric Quartz Crystal", *Chemical and Pharmaceutical Bulletin*, 1990, pp. 1117-1120, vol. 38, No. 5.

Karasek, F.W., "Cascade Particle Analyzer", *Chemical Abstracts*, 1979, abstract No. 11593, vol. 90, No. 2.

Kösslinger, C. et al., "Comparison of the Determination of Affinity Constants with Surface Plasmon Resonance and Quartz Crystal Microbalance", *Eurosensors XII. Proceedings of the 12th European Conference on Solid-State Tranducers and the 9th UK Conference on Sensors and Their Applications, Proceedings of Eurosensors Conference*, Southampton, UK, Sep. 13-16, 1998, pp. 845-848, vol. 2.

Torres, L.. et al., "A Quartz Crystal Microbalance to Determine Enthalpies of Sublimation at Intermediate Temperatures by the Knudsen Effusion Method", *Measurement Science and Technology*, 1994, pp. 51-54, vol. 5, No. 1.

Suleiman, A. A. et al., "Recent Developments in Piezoelectric Immunosensors", *Analyst*, 1994, pp. 2279-2282, vol. 119, No. 11.

Wang, A. W. et al., "A Silicon-Based Ultrasonic Immunoassay for Detection of Breast Cancer Antigens", *Sensors and Actuators*, 1998, pp. 13-21, vol. 49, Nos. 1-2.

Woodberry, M. E. et al., "Investigation of Accelerated Aging Characteristics of a SAW Filter", *Proc.-IEEE Ultrasonics Symposium*, 1997, pp. 55-60, vol. 1.

* cited by examiner

MEASUREMENT AND USE OF MOLECULAR INTERACTIONS

CROSS-REFERENCE TO A RELATED APPLICATION

This application is a continuation of application Ser. No. 09/700,485, filed Nov. 15, 2000, now U.S. Pat. No. 6,589,727; which is a National Stage Application of International Application Number PCT/GB00/01587 filed Apr. 25, 2000 and which claims priority to Great Britain Application No. 9909308.0, filed Apr. 22, 1999.

FIELD OF THE INVENTION

This invention relates to methods for measuring molecular interactions and for separating, sorting and sizing particles. In particular, this invention relates to measurement of the affinity between different binding partners, e.g. in an antibody-antigen interaction.

BACKGROUND TO THE INVENTION

Specific molecular recognition is a fundamental process, being the basis of enzyme-ligand interactions, antibody-antigen interactions and the binding of molecules to receptors. Molecular recognition is achieved through non-covalent interactions such as electrostatic interaction (hydrogen bonds) and hydrophobic interactions. Thermodynamic measurements of binding constants and free energy, enthalpy and entropy changes offer insight into the molecular basis of recognition, particularly when coupled with information from X-ray diffraction and, when possible, site-directed mutagenesis.

Direct measurement of the force of interaction has been made by atomic force microscopy (AFM) as well as surface force apparatus. While AFM is capable of measuring bond rupture forces, the technique has the disadvantage that only one measurement can be made at a time. To date, AFM has been used on avidin-biotin interactions (Florin et al, Science, 1995, 264:415), DNA hybridisation (Boland et al, PNAS, 1995; 92:5291), antibody-antigen interactions (Dammer et al, Biophys. J., 1996; 70:2437) and adhesion glycoproteins (Dammer et al, Science, 1995; 267:1173).

Separating biological molecules on the basis of their relative affinities for ligands is a well recognised technique. For example, in affinity chromatography, the components to be separated are passed down a column that contains a specific ligand. The component of interest binds preferentially and strongly to the column and is retained on the column while the other components are removed. The bound material may be eluted off the column at a later stage.

Separation technologies are an important part of many research experiments. Increasing the sensitivity or selectivity of these techniques is desirable.

Kolomenskii et al, J. Appl. Phys., 1998; 84(4):2404–10, discloses surface cleaning and adhesion studies conducted using laser-generated surface acoustic pulses. The pulses were at a low repetition rate (20 Hz) and constant energy. The procedure was conducted in vacuum, and therefore is not suitable for commercial exploitation. An optical microscope was used to detect the removal of particles and it was not possible to distinguish between particles of different size.

WO-A-98/45692 discloses the use of a piezoelectric crystal sensor for determining the formation/dissociation of clathrate hydrates. Kurosawa et al, Chem. Pharm. Bull, 1990; 38(5):1117–20, reports using such a sensor for the detection of agglutination of antibody-bearing latex. WO-A-98/40739 also discloses a sensor, including a plate on which specific binding entities are immobilised, for use in indicating the presence of cells in a medium. These sensors are used by measuring a change in resonance frequency at constant voltage.

At present, where possible, most viruses are detected by culture of the specimen in cells, since this method is sensitive although time-consuming. Direct detection of viral DNA or RNA in clinical samples can be achieved using PCR and specific primers tailored for the virus of interest. Since PCR involves an amplification step, cross-contamination is a major problem and it is difficult to establish reliable quantitative methods. Other direct methods include electron microscopy, immune electron microscopy, and methods based on antigen detection with enzyme-linked antibodies. These methods are often relatively insensitive and hence require relatively large quantities of the viral particles.

SUMMARY OF THE INVENTION

The present invention is based on the realisation that the bonds between a target molecule, or a target molecule attached to a particles, and a surface, can be ruptured by mechanically oscillating the surface at increasing amplitude, leading to detachment of the target molecule or particle from the surface. The required acceleration, and hence force, will depend on a variety of factors, including the mass of the molecule or particle, the nature of the bond to the surface and the geometric shape or size of the target molecule or particle. The present invention may therefore be used to separate or to size different target molecules, or to detect their presence.

According to a first aspect of the present invention, a method for separating a target analyte from a composition, comprises the steps of:
(i) contacting the composition with a binding partner for the analyte, the binding partner being immobilised on a surface; and
oscillating the surface at increasing amplitude, to selectively remove the analyte, or other components of the composition, from the surface.

In addition, the present invention may be used in a method for determining the presence or size of particles, or the affinity between binding partners. According to a second aspect of the invention, such a method comprises the steps of:
(i) contacting the binding partners, one of which is immobilised on a surface;
(ii) oscillating the surface at increasing amplitude; and
(iii) detecting a dissociation event.

In this second aspect, the invention may be applied to a variety of physical and chemical bonds, ranging from relatively weak interactions such as hydrogen bonds through to covalent bonds.

Apparatus suitable for use in the present invention comprises a surface having one binding partner immobilised thereon; means for oscillating the surface at increasing amplitude; and means for detecting a dissociation event. in particular, the apparatus may comprise an acoustic transducer device (ATD), e.g. a quartz crystal microbalance (QCM) or surface acoustic wave device, or any piezoelectric material which can be made to oscillate, e.g. by applying an alternating voltage or magnetic field. These are cheap devices compared to an AFM and can be multiplexed. Another advantage of using such apparatus is that the majority of bonds are broken simultaneously, giving rise to detectable sound and sharp noise peaks at specific accelerations (applied voltage to the ATD). Another advantage is that the ATD can be used as a sensitive microphone, to detect the acoustic emission when the dissociation event occurs.

In most prior art experiments using an ATD, changes in the resonant frequency or phase have been measured when the ATD is driven at constant voltage. In contrast, the present invention involves increasing the driving voltage and hence the amplitude of oscillation of the ATD.

The present invention has widespread applications for separation, sorting and sizing. The Examples show that, in air, streptavidin-labelled spheres can be separated from normal latex spheres using a QCM with a biotinylated surface and with a driving voltage above 0.1 V but below 6 V. The normal latex spheres are removed from the surface, leaving only the streptavidin-labelled spheres attached to the surface (by the stronger streptavidin-biotin bond) This opens up a new form of separation science based on variable force applied for a certain length of time, with application, for instance, in particle-sizing and sorting, cell-sorting, panning for phage as well as the design of new biosensors. Such a separation method is of low cost and can easily be multiplexed and automated. For instance, it is possible to deposit different targets at different positions on the same microbalance and screen a library of ligands against multiple targets simultaneously. Detection and analysis of viral particles, which are of fixed size, is another area of application. Equally importantly, this invention provides a new, sensitive and potentially quantitative tool, to probe the forces involved in molecular recognition.

DESCRIPTION OF THE INVENTION

Figure 1:
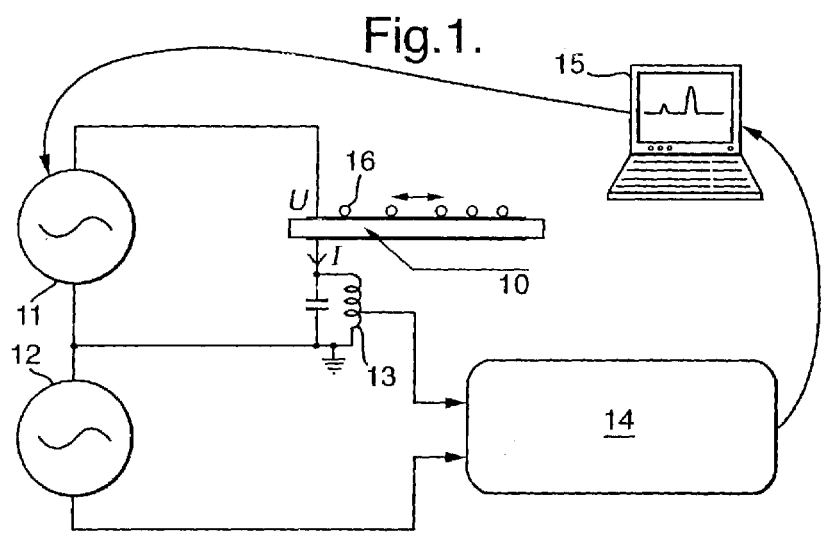
FIG. 1 shows a circuit comprising a piezoelectric transducer, a pure sinusoid f generator, a 3f+Δf generator, a 3f+Δf filter, a Lock-in amplifier and analog-to-digital converter, and a computer having a data input and a control output shown by the arrows.

The present invention makes use of sensor apparatus that can be made to oscillate. The sensor can be made to oscillate in a number of ways, e.g. by the of surface acoustic wave devices, resonance quartz crystal devices, acoustic plate mode and thin membrane flexible plate devices.

Many different sensors, suitable for use in the invention, are available from commercial sources. A description of sensors that may be used in the present invention is contained in Acoustic Wave Sensors, Ballantine et. al., (1997) Academic Press. The sensor is preferably a surface acoustic wave device, or, more preferably, a quartz crystal microbalance (QCM).

The QCM is typically a disc of disc of crystalline quartz with gold electrodes on the top and lower surfaces. It undergoes a shearing oscillation when an alternating voltage is applied to the electrodes, due to the converse piezoelectric effect. Increasing the voltage increases the amplitude of oscillation of the QCM.

The quartz crystal is also a sensitive microphone and can be used to detect acoustic omission due to the rupture event. It is technically easier to excite oscillations at a frequency corresponding to one major resonance frequency, and detecting acoustic emission near to another mode. As an example, the QCM is driven at its resonance frequency, and the acoustic emission is detected at its third harmonic.

For the purpose of illustration, the term "analyte" may be used to describe the binding partner or component that is contacted with the surface-immobilised binding partner. Following contact, the analyte is bound to the sensor via molecular interaction and subjected to acceleration and hence a force is exerted on the analyte. As the amplitude of oscillation increases, and at a particular threshold force, bond rupture occurs. A previously bound analyte particle is thus free to roll on the surface.

The analyte may be any microscopic entity that is capable of being retained on the sensor via a molecular interaction. The analyte may be a protein, antibody, antigen, enzyme, enzyme inhibitor or polynucleotide. The analyte may also be a larger particle, such as a bacterium, cell, virus, prion or phage. Further examples of particles that are particularly suited for use in the present invention include microspheres of any material, e.g. silica, gold or latex, or large macromolecules such as plasmids. The surface-immobilised binding partner may be of the same type, and may be chosen accordingly, and depending on the appropriate physical or chemical bond.

The dissociation of smaller analytes is preferably detected by acoustic emission. Larger particles may also be detected by optical means, e.g. microscopy.

In the first aspect of the invention, separation is carried out by immobilising the target molecule to a sensor surface via an interaction with a binding partner. The surface may then be oscillated to disrupt the molecules on the surface of the sensor. Oscillation is carried out by steadily increasing amplitude and therefore acceleration, and may be selected either to remove the target molecule from the surface, or to remove other components of the composition from the surface, leaving the target molecule bound to the surface. in a preferred embodiment, the sensor surface is oscillated by using a piezoelectric acoustic wave device, e.g. a QCM. The same piezoelectric device may be used as a microphone to detect acoustic noise produced by a rupture event.

The separation technique may be applied to select for molecules that interact strongly with a particular binding partner. For example, the technique may be applied to select cells with particular receptor molecules expressed at the cell surface, or to select for antibodies with strong affinity for a particular ligand.

Different ligands may be localized at different positions on the surface by, for example, contact printing or the use of masks or photolithography. It is then possible to screen a mixture for several strongly binding partners with several different ligands simultaneously. In particular, the invention can be used with chips having different materials such as receptors immobilized thereon. More generally, the chips can display materials that allow testing for different infections, pathogens, prions, food allergens, viruses, bacteria etc, e.g. in human and animal clinical testing, and for hygiene monitoring in food and water. Further, the invention can be used for library screening, phage display etc.

The second aspect of the present invention is a method for determining the presence or size of particles, or the affinity levels between molecules. Preferably, one molecule is immobilised to a sensor surface and the other is immobilised to a particle, e.g. a microsphere. The particle is then attached to the sensor via the molecular interaction of interest. The functionalised particles are then oscillated by applying a voltage to the sensor. As the amplitude of oscillation increases, the force reaches a critical value where bond rupture occurs. At this point, a characteristic noise may be detected by using a sensitive amplifier and the motion of the particles may be observed, e.g. under an optical microscope. The size of the signal depends on the number of particles bound to the sensor surface. Typically, if the QCM is used as described below, in Example 1, with physisorbed microspheres, noise is detected at 0.1–1V, dependent on the size of the microspheres, the onset occurring when the microspheres are observed to be sliding and escaping away, under the microscope. A plot may be made of noise generated versus amplitude (or applied voltage), which will be referred to as a rupture force spectrum. The point at which the bond ruptures will be apparent from the plot, as there will be a noise peak. Therefore, the critical voltage at which bond rupture occurs can be determined. Suitable calibration experiments, using particles having known bond densities and strengths, allow this method to be made quantitative. Further, the height of the acoustic emission peak is a measure of the number of bound particles.

The present invention may be used to study any molecular interaction, but is particularly suitable for the study of enzyme/ligand interactions, antibody/antigen interactions and receptor/ligand interactions or an interaction between a large macromolecule and its natural binding partner. The method may also be applied to the study of hybridisation events between polynucleotides. Thus, in the first aspect of the invention, the ligand may be, for example, a protein, an antibody or antigen, an enzyme, an enzyme inhibitor, a polynucleotide or a large macromolecule such as a large plasmid or virus. Either material may be bound to the surface or particle, in the second aspect of the invention.

The following Examples illustrate the invention.

In the Examples, rupture force spectroscopy is used to measure the adhesion forces between a surface and a small particle. This effect is based on oscillating a surface, with microparticles on it, at monotonously increasing amplitude and hence increasing acceleration. This is achieved by means of driving the surface with a piezoelectric acoustic wave device, in this case a quartz crystal microbalance (QCM). As the amplitude increases, so does the acceleration and hence the force exerted on the particle. The rupture of all the bonds attaching the particle to the surface results in acoustic noise and the same piezoelectric device is used as a sensitive microphone to detect this noise, produced by the rupture event. A schematic representation of the apparatus used in Examples 1 to 5 is shown in FIG. 1; a more general schematic representation of the preferred apparatus is shown in FIG. 8.

More specifically, FIG. 1 shows a circuit comprising a piezoelectric transducer 10, a pure sinusoid f generator 11, a 3f+Δf generator 12, a 3f+Δf filter 13, a Lock-in amplifier and analog-to-digital converter 14, and a computer 15 having a data input and a control output shown by the arrows. In Examples 1–5, f=14.2 MHz, and Δf is 82 kHz. Particles 16 are placed on the surface of the substrate.

Figure 8:
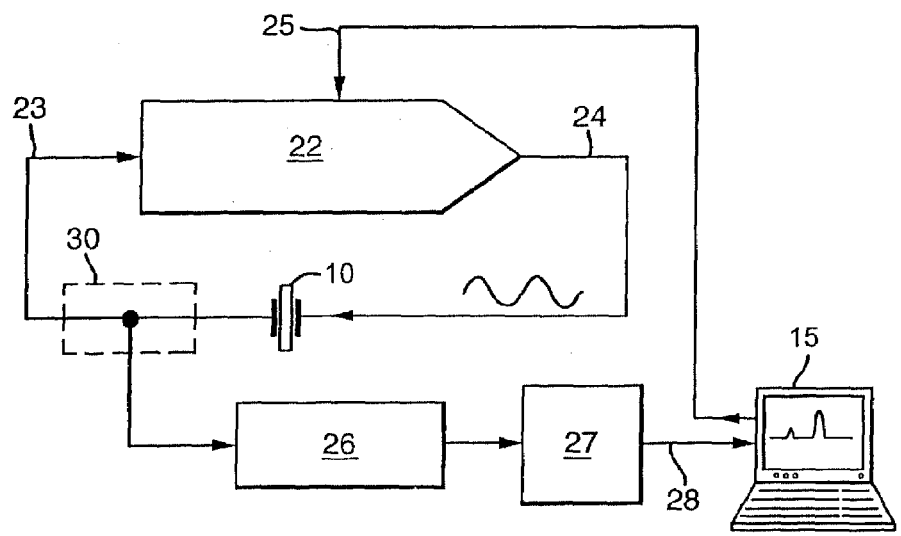
FIG. 8 shows a more general schematic representation of the preferred apparatus.

FIG. 8 shows a piezoelectric transducer 21 (such as QCM, SAW device, etc.), and a variable gain amplifier 22 with input 23 and output 24 capable of delivering smoothly rising output amplitude under control of a signal 25. The circuit also comprises a bandpass receiver 26 (for example similar to a SSB radio receiver), and an analog to digital converter or converters 27 supplying data via a link 28. Further, the circuit comprises a controller, recording and data signal processing device 29 (for example computer or specialised DSP processor). The contact indicated by a broken line 30 can be replaced by more optimised filtering and coupling means, e.g., it may be a passive L, C, R network.

In use of the circuit shown in FIG. 8, the amplifier 22 with transducer 10, together with optional filtering/coupling means 30, provides a simple oscillator network, oscillating preferably at a frequency where the transducer is efficient; for QCM it may be a resonance frequency. This oscillation frequency (F) is, e.g., 14 MHz. The amplitude of driving voltage at output 24 rises smoothly under the control of the controller 15 by means of the control link 25. The emerging signal of acoustic emission at point 30 may be purified by means of an optional filter/coupler and then fed to the input of the bandpass receiver 26. The working receiver frequency band may be selected by a maximum signal-to-noise criterion, e.g., the resonance mode located near to the third harmonic (3*F++ΔF), e.g., 42.082 MHz.

Single or quadrature output signals are converted by an analog to digital converter or converters 27 of high dynamic range. The data are then further digitally processed at 15 in order to extract useful signal, and then recorded and/or presented to the observer. The amplifier 22 may be additionally equipped with passive output and/or filter(s), improving the signal to noise ratio, and also ensuring that the oscillator works under the correct frequency and phase shift of current to voltage across the transducer.

Figure 9:
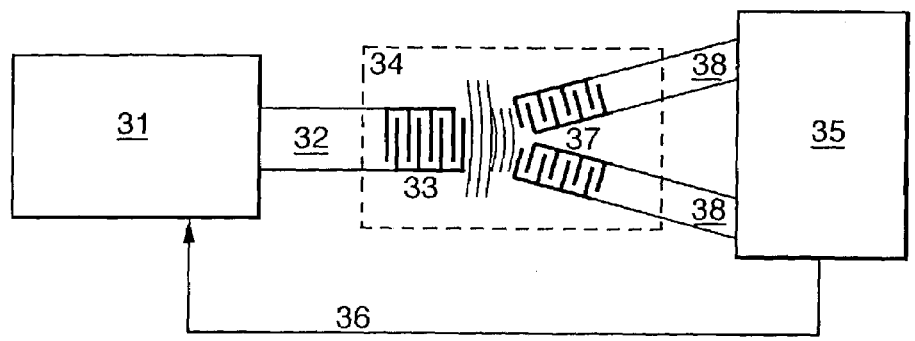
FIG. 9 shows a preferred SAW-based sensor for use in the present invention.
Figure 10:
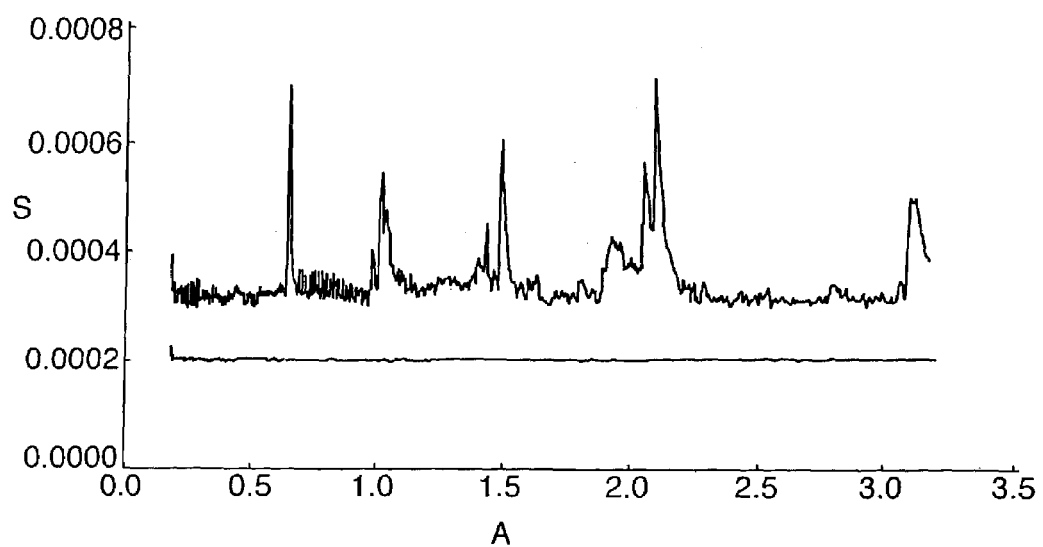
FIG. 10 shows plots of signal noise (5; arbitrary units) versus amplitude (A; volts).

FIG. 9 illustrates a preferred SAW-based sensor for use in the invention. It comprises means 31 for generating RF voltage at output 32 with increasing amplitude which drives transducer electrodes 33. The electrode arrangement 33 is optimised for the generation of high amplitude SAW at a piezo-substrate 34. The electrode arrangement 37 is optimised for best transduction of acoustic emission to an electrical signal. The pattern may be complex, comprising one or more pairs of electrodes. The device further comprises a control unit 35 for controlling the generator 31 by means of a link 36 and for receiving generated signals at one or more inputs 38 and performing data signal processing, e.g. correlation analysis.

Figure 4A:
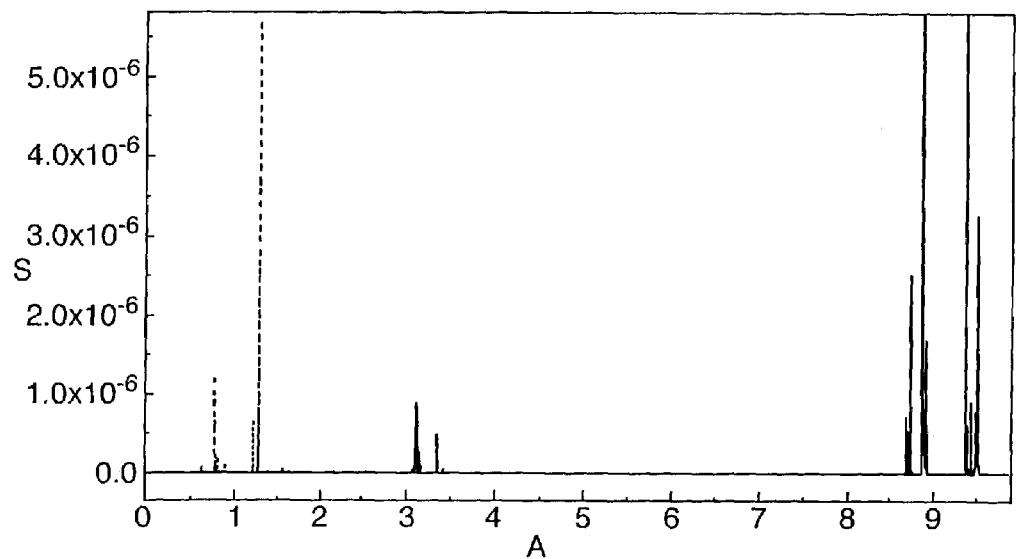
FIGS. 4A–D show plots of signal noise (S; arbitrary units) versus amplitude (A; volts).
Figure 4B:
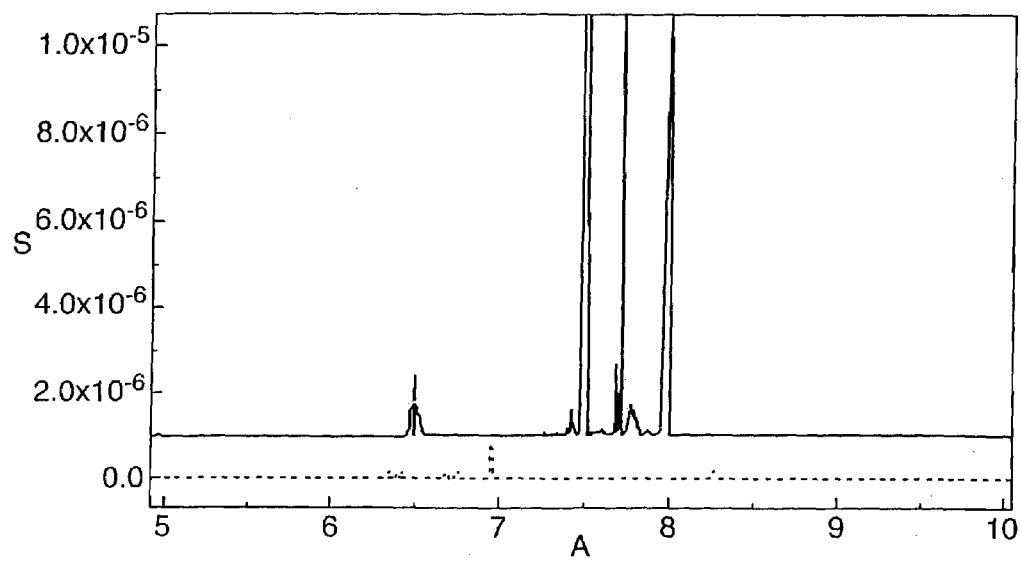
Figure 4C:
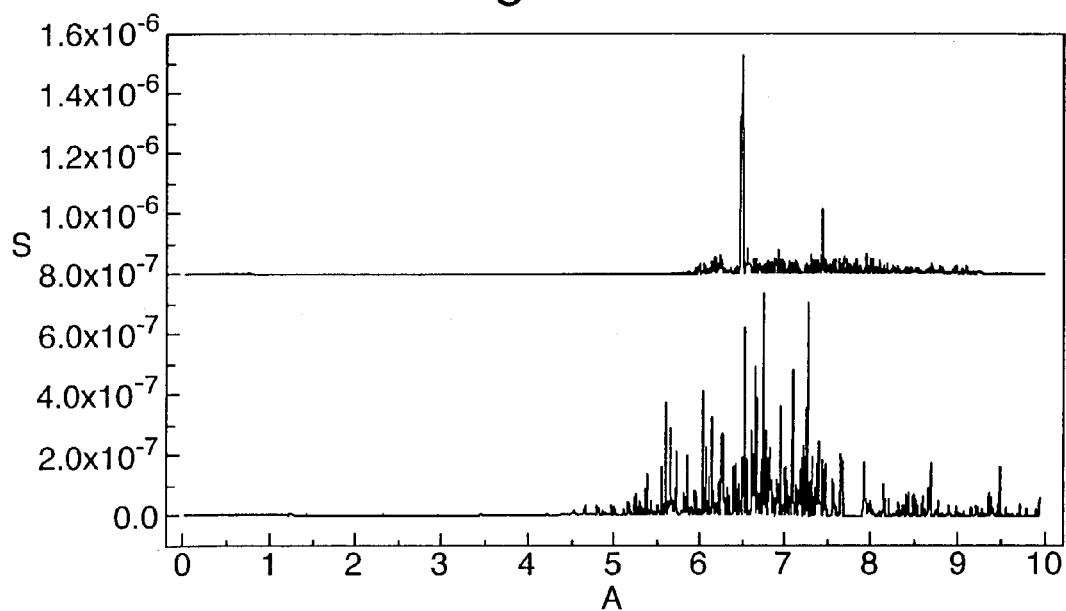
Figure 4D:
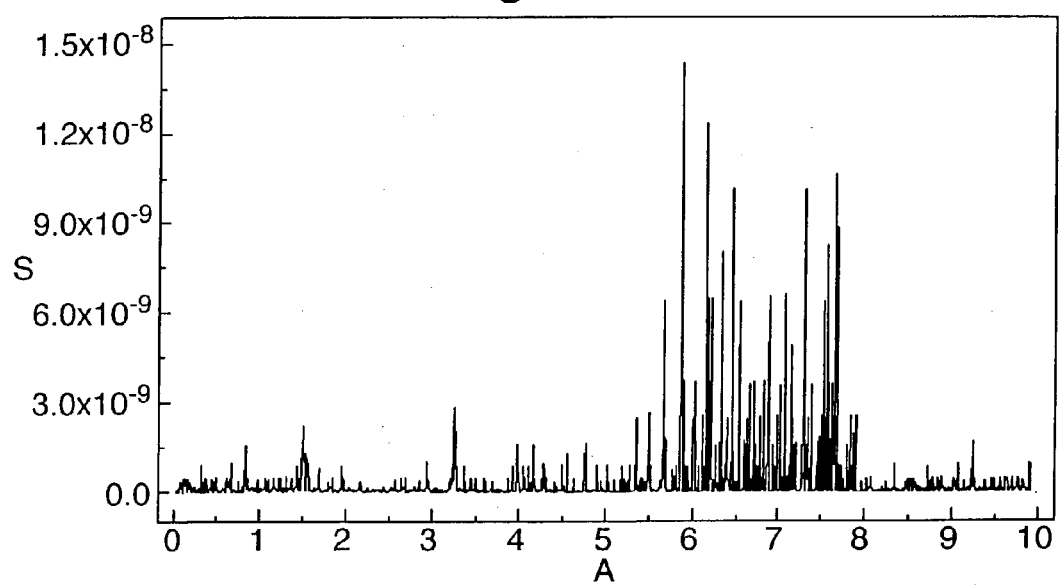
Figure 5A:
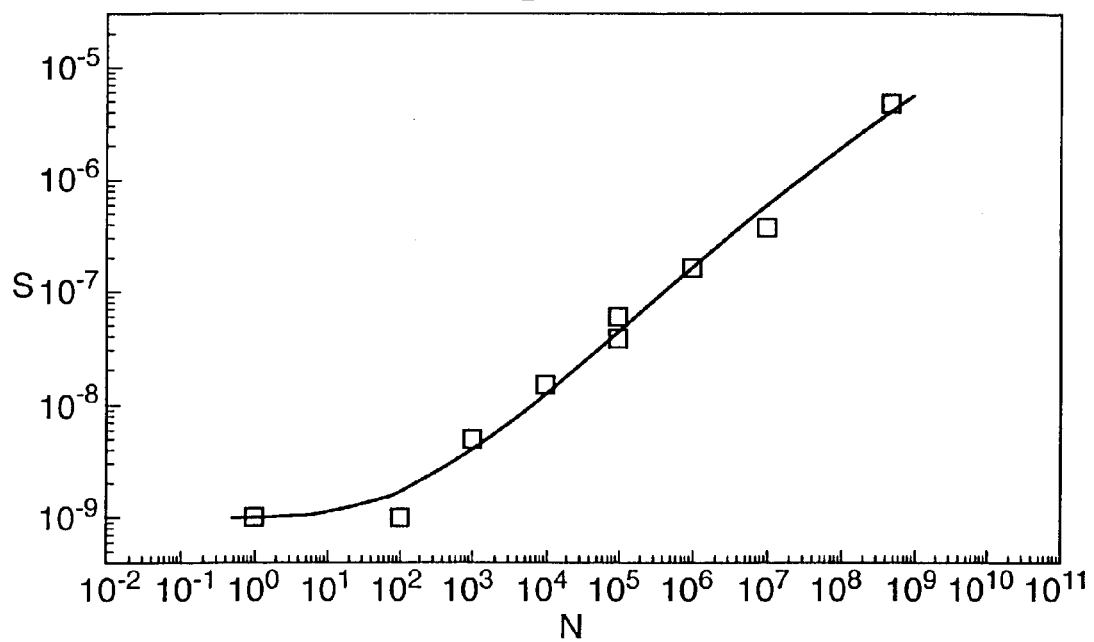
FIGS. 5A–B show plots of signal noise (S; arbitrary units) versus number of particles (N).
Figure 5B:
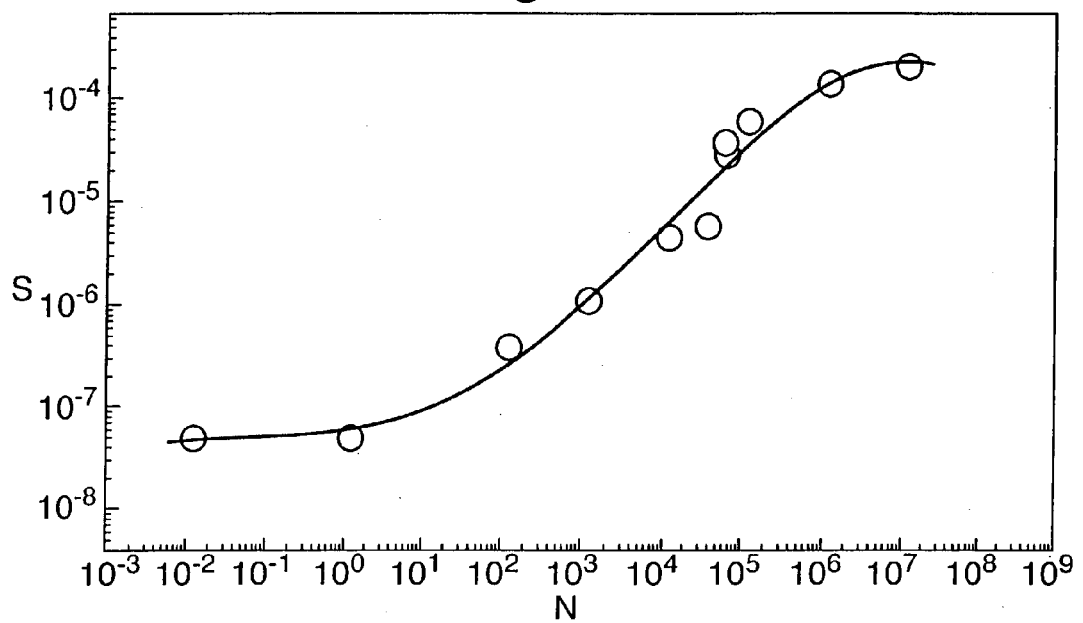
Figure 6A:
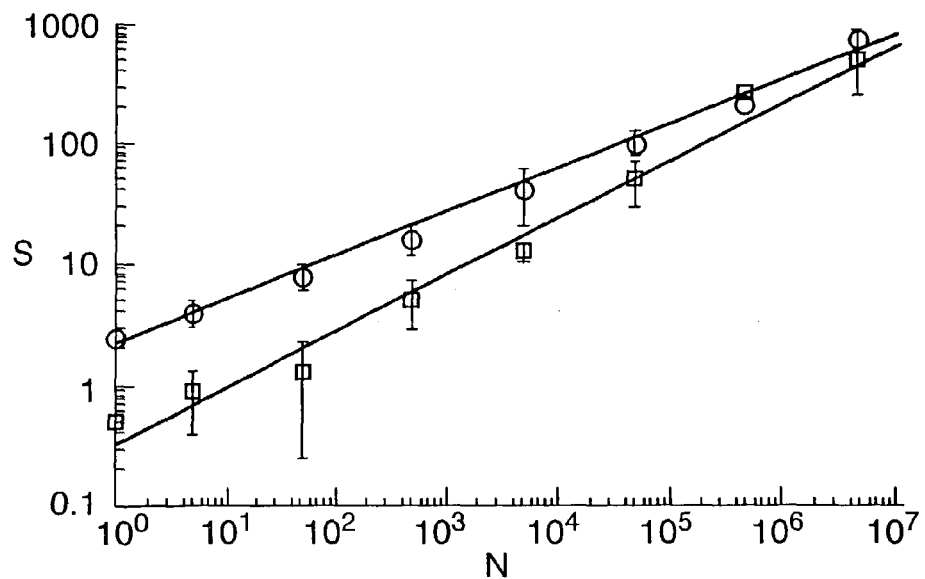
FIG. 6A shows plots of signal noise (S; arbitrary units) versus number of particles (N).

In use of the SAW-based sensor, the generator 31 generates RF voltage that is suitable for providing an efficient transducing frequency at output 32, and this is fed to generating transducer electrodes 33 located on the piezo-substrate 34 (dotted line). The amplitude of RF voltage rises over time under the control of the controller 35 by means of the control link 36. The receiving electrodes 37 transduce the acoustic emission that emerges from the active area to an electrical signal which is fed to the receiver/controller 35 and input(s) 38. The data obtained after analog to digital conversion then undergo signal processing in order to extract useful signals. Results are then finally recorded and/or presented to operator Certain results from the Examples are shown in FIGS. 2 to 7 and 10. FIGS. 2A, 2B, 3A, 3B, 4A, 4B, 4C, 4D, 6B, 7 and 10 are plots of signal noise (S; arbitrary units) versus amplitude (A; volts). FIGS. 5A, 5B, and 6A are plots of signal noise (5; arbitrary units) versus number of particles (N).

BSA: Bovine serum albumin
LB: Luria broth
DIC: Dimethylaminoisopropyl chloride
DMAP: Dimethylaminopyridine
EDC: 1,3-dimethylaminopropyl-3-ethylcarbodiimide
NHS: N-hydroxysuccinimide
PBS: phosphate-buffered saline

EXAMPLE 1

Latex spheres, 5 μm diameter, were attached to a QCM sensor surface via multiple numbers of the bond of interest. The coverage of the spheres used was 1% of the surface area of the QCM. The spheres had only 1% variation in their diameter.

The QCM sensor comprised polished quartz plates, acoustic traverse-cut at 35°, and 8.25 mm in diameter. Layers of chromium (20–30 nm thick) and then gold (100–120 nm thick) were deposited.

Three different bonds were studied, in experiments conducted in air: a physical bond (latex-gold), a streptavidin-biotin bond and a covalent bond (amide linkage). The physical bond was made by placing the latex spheres directly on the sensor surface and drying in nitrogen. The streptavidin-biotin bond was made by applying biotinylated BSA to the surface, and drying in nitrogen. The chemical bond was made by forming a thiol monolayer using an acid-terminated thiol (12-mercaptododecanoic acid) dissolved in ethanol; this was then activated using EDC-NHS, and the amine terminated spheres were added to form the amide bond.

The experiments were performed in a chamber equipped with two optical windows: one to provide laser illumination of the sample, and the other to allow observation of the scattered laser light by an optical microscope. The QCM was is placed in the chamber. A signal generator, Model DS345 (Stanford Research Systems), was used to drive the QCM. Motion and detachment of particles were observed using an Olympus BH-2 optical microscope equipped with a CCD Panasonic WL-SL300 video camera. The main measuring device was a Lock-in amplifier, SR 844 (Stanford Research Systems). The reference signal was fed to the Lock-in using a second generator synchronised to the first one. All devices were interfaced to a computer for control of the experiment and collection of the data.

Figure 2A:
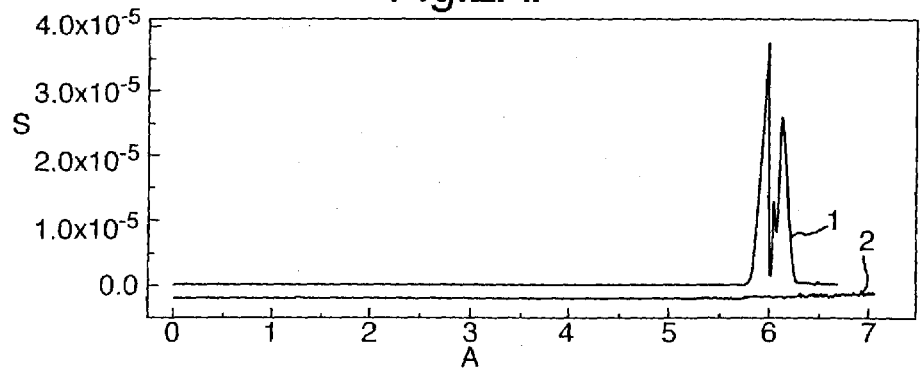
FIGS. 2A–B show plots of signal noise (S; arbitrary units) versus amplitude (A; volts).
Figure 2B:
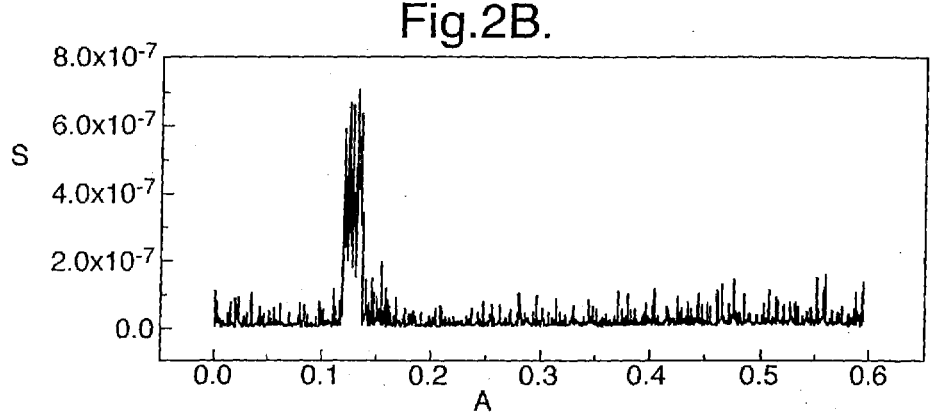

FIG. 2A shows the rupture force spectra for streptavidin-biotin (1) and the chemical bond (2); FIG. 2B is the spectrum for the physical bond.

By recording the rupture force spectra, it is possible to determine experimentally the force or voltage required to break the bonds. This can be used for separation. As shown in FIG. 2A, if there is a mixture of 5 μm spheres, some of which have streptavidin on the surface and some which do not, then by applying a voltage above 0.1 V but below 6 V, say 1 V, to a QCM with biotin on the surface, it is possible to separate the two sets of spheres to provide only streptavidin-labelled spheres on the surfaces. This technique may also be used to detect streptavidin-labelled spheres, since only these spheres would bind to the surface if oscillated at 1 V.

To make the measurement quantitative, the amplitude of oscillation of the QCM has been calculated at different voltages, based on experimental data, allowing estimation of the force on the microsphere. This estimate was performed by measuring the power consumption of the QCM and its Q factor (or merit factor–the reciprocal relative resonance bandwidth=$f/\Delta f_{resonance}$). The amplitude A is given by:

$$A=[QP/2\Pi^3 f^3 M]^{1/2}$$

where Q is the Q or merit factor, P is the electrical power consumed by the QCM, f is the resonant frequency of the quartz crystal and M is the effective mass of the QCM quartz plate involved in motion. The Q factor was determined to be c. 15000 at 6V, which gives an estimate of the vibrational amplitude of the QCM of 60 nm. The force on the sphere is therefore 9 μN. This should be compared to the force needed to break a single streptavidin-biotin bond of 160 pN[2] and indicates that approximately 60,000 bonds are broken simultaneously. Estimation indicates that this corresponds to 50% or more of the initial streptavidin-biotin bonds between the sphere and the surface. This means that the majority of the bonds attaching the spheres to the surface are broken simultaneously. This gives rise to the sharp peaks observed in the rupture force spectra and the detectable noise on bond breakage.

EXAMPLE 2

This Example shows that methods of the invention may also be carried out in solution. The Q factor of the QCM will decrease due to liquid loading, thus reducing the amplitude of oscillation at a particular voltage when compared to air. There will be viscous forces acting on the microsphere and its effective mass will increase, due to the associated layer of water, increasing the force on the sphere.

Figure 3A:
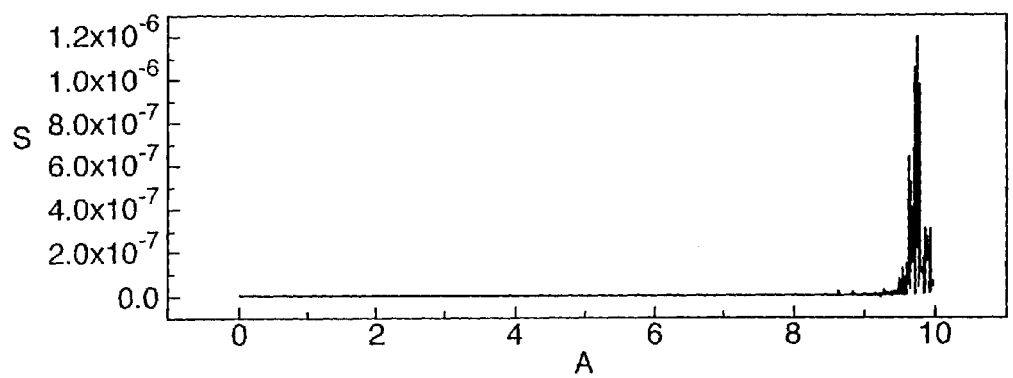
FIG. 3A–B show plots of signal noise (S; arbitrary units) versus amplitude (A; volts).
Figure 3B:
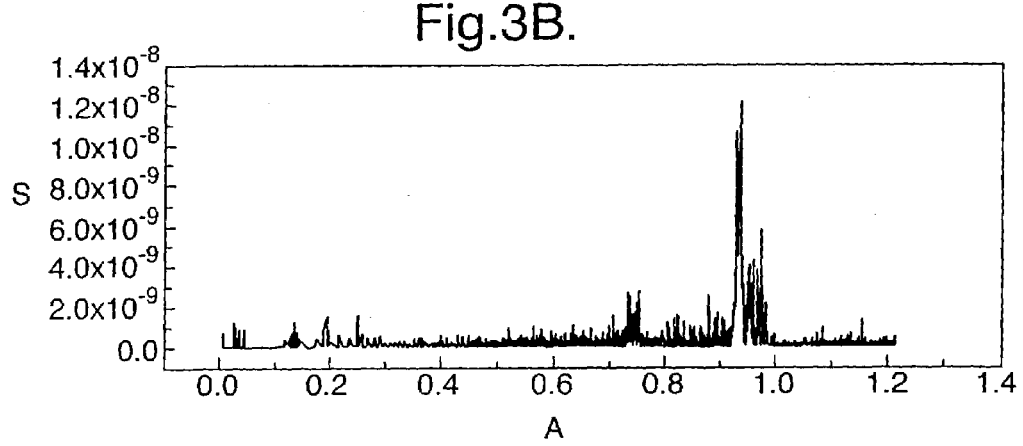

FIG. 3 shows the rupture force spectra for 5 μm latex spheres attached to the surface via streptavidin-biotin (FIG. 3A) and a chemical bond (FIG. 3B). Rupture occurs respectively at 1 V and 10 V.

A reduction in the critical voltage for the streptavidin-biotin bond, by a factor of six, from 6V to 1V on going from air to water, and the breakage of the chemical bond in water, indicates that the latter effect is dominant. Thus, this Example clearly demonstrates that bond-breaking, and hence separating and biosensing, are possible in water liquid or another.

Assuming that the bond density for the physical, streptavidin-biotin and chemical bonds is the same and since the same size microspheres have been used in these experiments, a relative scale of rupture force can be obtained. This is 1:60:600 for the physical:streptavidin-biotin:chemical bond. This scaling appears reasonable and demonstrates the dynamic range of this method. By conducting suitable calibration experiments with known bond densities, it should be possible to make these measurements quantitative.

EXAMPLE 3

The Example demonstrates the detection of viruses, and in particular genetically modified bacteriophage displaying a maltose-binding protein fused to the phage pill coat protein, since both the phage and the maltose-binding interaction are well characterised and readily available. The phage is a long, thin, filamentous virus consisting of a flexible rod 1 μm long and 6 μm in diameter. The genetically modified phage additionally display up to 5 maltose-binding proteins at one end of the virus as fusions to the phage pill coat protein, see McCafferty et al, Nature, 1990, 348:552. These phage can be specifically purified on amylose resin.

A maltose-binding protein fusion to the amino terminus of indole glycerol phosphate synthase was displayed on the surface of fd phage as a fusion to the amino terminus of the gene III-encoded coat protein. For this purpose, an fd phage vector, pJB113, was constructed; it encoded a genetic fusion between MalE (*E. coli*), trpC (*E. coli*) and gene III. This phage vector carried a tetracycline-resistance marker. The unmodified competitor phage was VCS M13 K07 helper phage (Stratagene) carrying a kanamycin-resistance marker.

Bacteriophage concentrations of $1\times10^{12}$ cfu/mL were obtained by infecting a 3 mL mid log phase LB culture of *Escherichia coli* strain TG1 with 10 μL of phage stock. After 2 hours of shaking (250 rpm) at 37° C., 1 mL of culture was inoculated into 100 ml LB and shaken at 350 rpm, 37° C. for 1 hour. Tetracycline (10 μg/mL) or kanamycin (50 μg/mL) was added to the pJB113 or VCS culture, respectively, which was grown overnight at 30° C., 250 rpm. Bacteria were pelleted (15 mins, 4.1 krpm) and the phage precipitated from the supernatant by addition of NaCl and PEG6000 to final concentrations of 0.5 M and 4% (v/v) respectively. After standing for 1 hour on ice, the phage were recovered by centrifugation (30 mins, 4.1 krpm) and the phage pellet was resuspended in 1 ml $H_2O$ and stored at 4° C.

Soluble starch (500 mg, 0.01 mmol, 1 eq.) was dissolved in DMF (10 ml) and stirred for 5 min (partially soluble). To 11-mercaptododecanoic acid (11.5 mg, 0.05 mmol, 5 eq.) in DMF (0.5 ml) was added DIC (7.8 μl 6.3 mg, 0.05 mmol, 5 eq.) and DMAP (cat.) and this solution was added to the starch solution. The reaction was left stirring at room temperature overnight. The reaction was then purified using a stirred cell with a 10000 MW membrane cut-off, by rinsing the solution with milliQ water (6 times 50 mL) and concentration, followed by lyophilisation overnight.

The surface was prepared using the modified starch containing a thiol group so that it could be chemically coupled to the surface. The QCM (prepared as in Example 1) was placed in a solution of the starch in methanol (1 μg per mL) for 12 hours. The samples were then washed and dried under a stream of nitrogen. The viruses were deposited on the surface from solution and dried at room temperature for experiments in air. Different virus concentrations were made by dilution. To perform the experiments with maltose blocking the maltose-binding protein, 100 nM maltose was added to the solution of phage.

The surface of the QCM was thus coated with a layer of soluble potato starch (which contains branched polymers of maltose), chemically attached to the gold surface via a sulphur-gold bond. Experiments were performed in both air and water.

FIG. 4A shows the rupture force spectrum obtained in water for an equal mixture of maltose-binding phage (–) and unmodified phage ( . . . ), the scan being acquired over 500 seconds. There are approximately 500 million of each type of phage on the surface of the gold electrode. For the unmodified and hence non-specifically bound phage, a rupture peak was detected at 1.2 V. The corresponding rupture peaks for the maltose-binding were around 9 V and are more intense than the non-specifically bound phage due to the greater energy released on bond breakage. In air, no peaks from the specifically bound maltose-binding phage were observed up to 10 V; FIG. 4B shows the data in air for just the non-specifically bound phage. The peak occurs at 7.5 V, an increase of approximately 6 over the peak found in water. A second scan ( . . . ) has almost no peaks, indicating that the phage have been removed from the surface. This confirms that the additional viscous friction forces and the increase in effective mass of the particle make it easier to rupture the bonds between the phage particles and the surface in water than in air.

The sharpness of the peaks in the rupture force spectrum is apparently linked to the observation that the bond rupture occurs at a threshold voltage; this results in the acoustic noise occurring in a short time period and hence makes the method very sensitive. In addition, the signal from the specific binding phage is well separated from the non-specific binding phage and at higher amplitude, which means that non-specific adsorption does not affect the measurement of specific adsorption. A much larger force is required to rupture the specific interaction between the maltose-binding proteins displayed on the phage and the starch-coated surface compared to that required to rupture the non-specific interactions between unmodified phage and the surface.

FIG. 4C shows the result of a control experiment performed in air with the maltose-binding phage when its binding site is blocked with maltose and the phage are then deposited on the QCM at the centre (top plot) or over the whole surface (bottom plot); this showed similar behaviour to the unmodified phage, confirming that the difference is due to these specific interactions. FIG. 4D shows the rupture force spectrum in water with only 1000 phage on the surface, and indicates that the rupture event is still detectable. There is a small shift in peak position due to smaller changes in the Q or quality factor of the QCM, as a result of the change in loading.

The data also suggest that it should be possible to separate the non-specifically bound page from the maltose-binding phage by driving the QCM at a voltage above that for rupturing the bonds to the non-specifically bound phage but below that for the maltose-binding phage. This suggests an alternative way to screen phage libraries for binding, in which the binding affinity of the phage left on the surface is controlled by controlling the size of the applied voltage and the time for which it is applied, provided that the phage remain viable.

To determine the sensitivity of the method, a dilution experiment was performed, with the maltose-binding phage in water. FIG. 5A shows (for the most intense noise peaks near 9 V) that the power of the signal is linear with the number of phage over at least five orders of magnitude and that the presence of approximately 200 phage on the QCM can be detected with 99% probability. FIG. 5B shows a similar curve for the non-specific binding phage in air, indicating a detection sensitivity of 100 phage with 99% probability. The number of maltose-binding phage on the surface at low dilution was confirmed by direct imaging using an AFM.

This Example shows that the number of phage on the QCM surface may be detected. By contrast, using PCR, the number of copies of viral DNA is detected in solution. If it is assumed that all the virus particles in the solution sample will bind to the surface, which will occur if there is either a strong virus-surface interaction or the solution is allowed to evaporate leaving the viruses on the surface, then direct comparison of sensitivity is possible. The sensitivity of PCR is about 100 copies of viral DNA per mL which is comparable to detection sensitivity for the phage, by this Example (which is not optimised). The electronics may be improved, and there is scope to improve the sensitivity further, by possibly at least an order of magnitude. For example, in these experiments, the phage were deposited uniformly over the surface of the QCM. However both the amplitude and sensitivity of the QCM have a spatial dependence which means that the dominant signal comes from the centre of the QCM (as shown in FIG. 4C). This means fewer and hence more intense peaks could be recorded if the phage were only deposited in the centre of the QCM, resulting in an improvement in sensitivity.

This method can be straightforwardly extended to the detection of human viruses by the use of specific antibodies to the virus attached to the surface of the QCM. These antibodies form specific interactions between the virus attached to the surface of the QCM. These antibodies form specific interactions between the virus and the surface which can be broken at a particular surface acceleration. Non-specific adsorption by similar size or larger particles present in the sample will result in peaks at low voltage, as has now been shown, and this should not affect the analysis although adsorption by macromolecules onto the surface may reduce the number of antibodies available for binding to the virus. Most common viruses have a larger effective mass than the phage used in this Example although the number and strength of the specific interactions with the surface will be different. This means that the voltage required should be of a similar magnitude or smaller.

This Example shows that rupture force spectroscopy requires no amplification step, is quantitative, and has the potential to be immediate and low cost. This could lead to the rapid diagnosis of viral infection in many situations including patients in a clinical environment or plants and animals in agriculture.

EXAMPLE 4

This Example illustrates a virus binding assay. For this assay, quartz crystal microbalance chips were made from polished quartz plates, AT cut at an angle of 35° C. (HyQ, Cambridge, UK) and were coated in an Edwards vapour depositor with a 30 nm thick adhesion layer of chromium, then a 200 nm layer of gold as determined by calibrated electrical conductance. These chips were then immersed in a 1 mM solution of mercaptododecanoic acid in spectroscopic grade ethanol for 18 h, rinsed exhaustively with ethanol and then with water, and then blown dry under a stream of nitrogen. These chips were then immersed in a mixture of NHS (100 mM) and EDC (400 mM) for 20 min. They were rinsed exhaustively with water, then immersed for 1 h in a 50 µg/ml solution of mouse monoclonal IgG antibody raised against HSV I glycoprotein D in 10 mM PBS at pH 7.0. They were then rinsed with water and immersed for 10 min in a 1 M solution of ethanolamine at pH 8.5. They were then rinsed exhaustively with water and stored at 4° C. in 1 ml of PBS.

The number of viral particles/ml in a Ficoll-purified virus stock solution was determined using electron microscopy with an internal standard of latex spheres. Serial ten-fold dilutions of a HSV gD$^+$ stock solution at a concentration of $5 \times 10^{10}$ viral particles/ml were made in PBS (10 mM Na$_2$HPO$_4$/NaH$_2$PO$_4$, 2.7 mM KCl, 120 mM NaCl, pH 7.4) containing BSA (0.1 mg/ml) and stored at 4° C. The QCM chips were then mounted with solderless contacts in the instrument and either 1 µl or 40 µl of each of these dilutions was placed upon the chip surface coated with the anti-gD IgG antibody. After 40 min., the surface was washed thoroughly with water, then covered with 40 µl of PBS and the QCM scanned from 0–10 V.

Figure 6B:
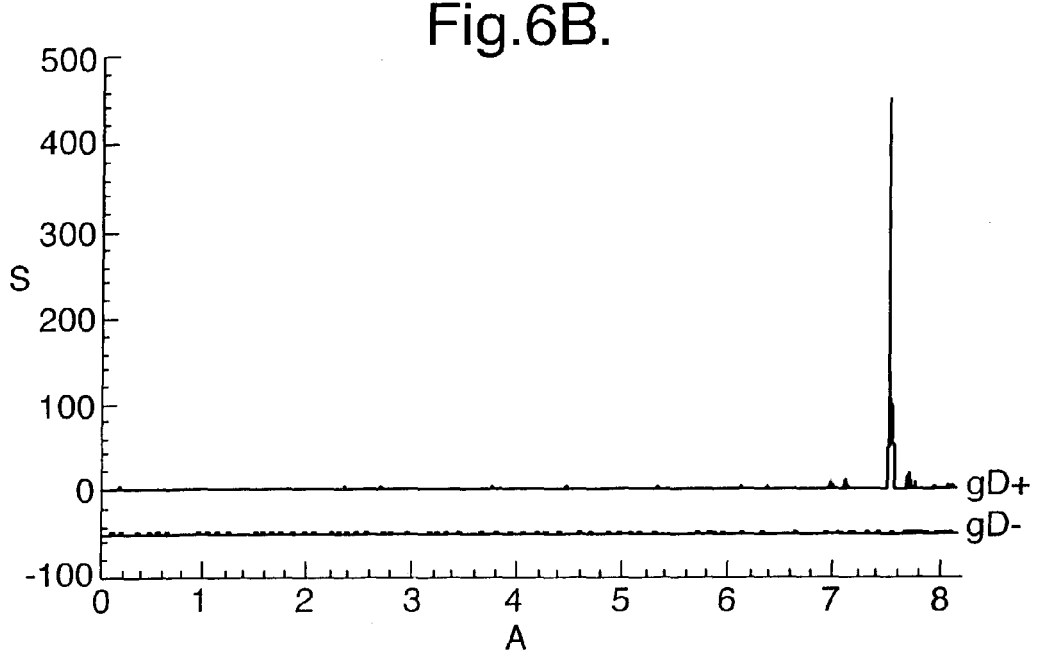
FIG. 6B shows (S; arbitrary units) versus amplitude (A; volts).

Results are shown in FIG. 6. FIG. 6A is a plot of signal (noise peak near 7.5 V) versus the number of gD$^+$ herpes simplex virus particles for the 1 µl (○) and 40 µl (□) samples; the line purity is good. FIG. 6B is a plot of noise versus amplitude for the gD$^+$ and gD$^-$ virus. The gD$^-$ virus, which has no specific interaction with the antibody on the surface, shows no peak: in contrast, the gD+ virus shows a sharp peak near 7.5 V.

EXAMPLE 5

For this bacterial binding assay, QCM chips were prepared as in Example 4. *E. coli* and *S. aureus* (laboratory strains) were cultured in brain heart/0.5% yeast extract broth and incubated overnight at 37° C. A 1 ml sample of each culture was adjusted to a concentration of $10^{10}$ cfu/ml as determined by optical density, and centrifuged at 12,000 g for 2 min; the pellet was re-suspended in sterile PBS. 10 µl of the bacterial suspension was placed upon a QCM chip coated with an anti-*E. coli* IgG antibody in a manner similar to that described in Example 4 for the anti-HSV antibody. After 40 min., the surface was washed thoroughly with water, covered with 40 µl of PBS and the QCM then scanned from 0–10 V.

Figure 7:
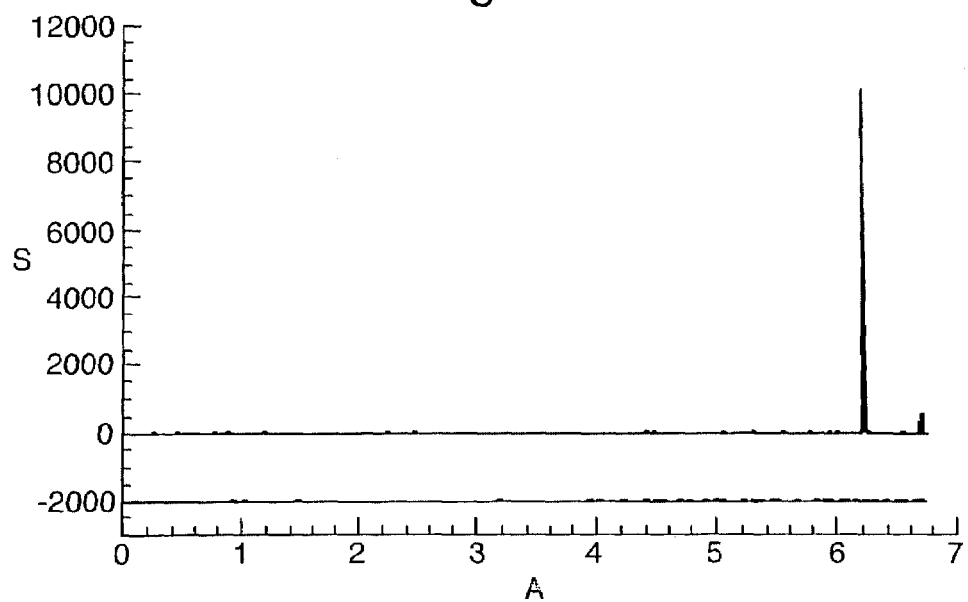
FIG. 7 shows plots of signal noise (S; arbitrary units) versus amplitude (A; volts).

Results are shown in FIG. 7. The noise/amplitude plot shows a sharp signal at about 6 V for *E. coli*, and none for *S. aureus*.

EXAMPLE 6

In this Example, a SAW device, as shown in FIG. 9, was used. In this case, a single instrument (HP8512a, Hewlett Packard) was used which combines an amplifier 1 and receiver and controller 5 in a single instrument. The instrument is set to a Continuous Wave and Power Sweep mode. The SAW device was the commercially available RF1171 from RF Monolitics, Inc. About 100,00 latex spheres, 1 µm in diameter were deposited on the surface of the SAW. The resulting spectrum is presented in FIG. 10. A number of peaks are observed, that are not present on the clean surface. This shows that a SAWS device can be used to detect the rupture event. The different peaks probably correspond to clusters of spheres on the surface of different sizes and hence the peaks are observed at different positions.

We claim:

1. An apparatus suitable for detecting the dissociation of a bond, which comprises:
   (i) a surface on which the bond may be formed;
   (ii) a means for oscillating said surface at monotonously increasing amplitude in the plane of said surface, and
   (iii) a means for detecting a dissociation event.

2. The apparatus of claim 1, wherein one or more ligands are immobilized on the surface.

3. The apparatus according to claim 2, wherein said one or more immobilized ligands are selected from the group consisting of cells, bacteria, viruses, prions and phages.

4. The apparatus according to claim 2, wherein different ligands are immobilized at different positions on said surface.

5. The apparatus according to claim 1, wherein said one or more immobilized ligands are selected from the group consisting of proteins, antibodies, antigens, enzymes, enzyme inhibitors and polynucleotides.

6. The apparatus according to claim 1, wherein said detecting means detects acoustic emission.

7. The apparatus according to claim 1, wherein said oscillating means and said detecting means comprise a piezoelectric or an acoustic transducer.

8. The apparatus according to claim 7, wherein said transducer is a surface acoustic wave device.

9. The apparatus according to claim 7, wherein said transducer is a surface crystal microbalance (QCM).

10. The apparatus according to claim 9, wherein said oscillating means drives the QCM at its resonance frequency, and said detecting means is sensitive to the acoustic emission at the third harmonic of the driving frequency.

11. The apparatus according to claim 10, wherein said oscillating means causes oscillation of the surface at one resonant frequency and said detecting means detects dissociation at another frequency.

12. The apparatus according to claim 11, wherein said another frequency is another resonant frequency.

13. The apparatus according to claim 11, wherein said oscillation frequency is the fundamental resonant frequency.

14. The apparatus according to claim 13, wherein said another frequency is the third overtone resonant frequency.

15. The apparatus according to claim 11, wherein said oscillating means drives the QCM at its resonance frequency, and said detecting means is sensitive to the acoustic emission at the third harmonic of the driving frequency.

16. The apparatus according to claim 1, wherein said oscillating means causes oscillation of the surface at one resonant frequency and said detecting means detects dissociation at another frequency.

17. The apparatus according to claim 16, wherein said another frequency is another resonant frequency.

18. The apparatus according to claim 16, wherein said oscillation frequency is the fundamental resonant frequency.

19. The apparatus according to claim 18, wherein said another frequency is the third overtone resonant frequency.

20. An apparatus suitable for detecting the dissociation of a bond, which comprises:
   (i) a surface on which the bond may be formed;
   (ii) a means for oscillating said surface at increasing amplitude in the plane of said surface; and
   (iii) a means for detecting a change in amplitude of another, simultaneous oscillation of said oscillating means caused by a dissociation event.

21. The apparatus of claim 20, wherein one or more ligands are immobilized on the surface.

22. The apparatus according to claim 21, wherein said one or more immobilized ligands are selected from the group consisting of proteins, antibodies, antigens, enzymes, enzyme inhibitors and polynucleotides.

23. The apparatus according to claim 21, wherein said one or more immobilized ligands are selected from the group consisting of cells, bacteria, viruses, prions and phages.

24. The apparatus according to claim 21, wherein different ligands are immobilized at different positions on the surface.

25. The apparatus according to claim 20, wherein said detecting means detects acoustic emission.

26. The apparatus according to claim 20, wherein said oscillating means and said detecting means comprise a piezoelectric or an acoustic transducer.

27. The apparatus according to claim 26, wherein said transducer is a surface acoustic wave device.

28. The apparatus according to claim 26, wherein said transducer is a quartz crystal microbalance (QCM).

29. The apparatus according to claim 20, wherein said increasing amplitude is monotonously increasing.

30. An apparatus suitable for detecting the dissociation of a bond, which comprises:
   (i) a surface on which the bond may be formed;
   (ii) a means for oscillating said surface at monotonously increasing amplitude in the plane of said surface, and
   (iii) a means for detecting a dissociation event;
wherein the means for detecting the dissociation event comprises detecting a signal other than the signal driving the oscillation of the surface.

31. The apparatus, according to claim 30, wherein said detecting means detects acoustic emission.

32. An apparatus suitable for detecting the dissociation of a bond, which comprises:
   (i) a surface on which the bond may be formed;
   (ii) a means for oscillating said surface at monotonously increasing amplitude in the plane of said surface, and
   (iii) a means for detecting a dissociation event;
wherein said detecting means detects acoustic emission.

33. An apparatus suitable for detecting the dissociation of a bond, which comprises:
   (i) a surface on which the bond may be formed;
   (ii) a means for oscillating said surface at monotonously increasing amplitude in the plane of said surface, and
   (iii) a means for detecting a dissociation event;
wherein said detecting means detects optical emissions.

* * * * *

UNITED STATES PATENT AND TRADEMARK OFFICE
CERTIFICATE OF CORRECTION

PATENT NO. : 7,195,909 B2 Page 1 of 1
APPLICATION NO. : 10/350892
DATED : March 27, 2007
INVENTOR(S) : David Klenerman et al.

It is certified that error appears in the above-identified patent and that said Letters Patent is hereby corrected as shown below:

Column 13,
Line 4, "a surface crystal" should read --a quartz crystal--.

Signed and Sealed this

Eighteenth Day of March, 2008

JON W. DUDAS
*Director of the United States Patent and Trademark Office*